United States Patent [19]
Bijl et al.

[11] Patent Number: 6,166,230
[45] Date of Patent: Dec. 26, 2000

[54] STEROL EXTRACTION WITH POLAR SOLVENT TO GIVE LOW STEROL, HIGH TRIGLYCERIDE, MICROBIAL OIL

[75] Inventors: Hendrik Louis Bijl, Vlaardingen; Johannes Hendrik Wolf, Delft; Albert Schaap, Barendrecht, all of Netherlands

[73] Assignee: Gist-brocades B.V., Ma Delft, Netherlands

[21] Appl. No.: 09/180,780

[22] PCT Filed: May 15, 1997

[86] PCT No.: PCT/EP97/02510

§ 371 Date: Feb. 8, 1999

§ 102(e) Date: Feb. 8, 1999

[87] PCT Pub. No.: WO97/43362

PCT Pub. Date: Nov. 20, 1997

[30] Foreign Application Priority Data

May 15, 1996 [EP] European Pat. Off. .............. 96201319

[51] Int. Cl.⁷ ..................................................... C07C 53/00
[52] U.S. Cl. .................................................................. 554/1
[58] Field of Search ................................. 554/8, 20, 206; 435/134

[56] References Cited

FOREIGN PATENT DOCUMENTS

86/04354  7/1986  WIPO ............................... C11B 1/10

OTHER PUBLICATIONS

Japan Abstr. of JP62/65689, 1987.
Derwent Abstr. of JP62/798598, 1987.
Yamada, "Production of Dihomo–γ–linolenic Acid, Arachidonic Acid and Eicosapentaenoic Acid by Filamentous Fungi", *Industrial Applications of Single Cell Oils,* Eds. Kyle and Rathledge, (1992) 118–138.

*Primary Examiner*—Deborah D. Carr
*Attorney, Agent, or Firm*—Morrison & Foerster, LLP

[57] ABSTRACT

The present invention relates to a process of treating an oil, the process comprising contacting the oil with a polar solvent to extract at least one compound that is soluble in the solvent, and then separating the solvent containing the compound from the so treated oil. The oil is microbially derived, and extracted either from a fermentation broth or a filtrate thereof using hexane. The compound to be extracted is usually a sterol or a diglyceride. The solvent is ethanol having up to 5% water. The oil can contain a polyunsaturated fatty acid such as C18, C20 or C22 ω-3 or ω-6 fatty acid, such as arachidonic acid.

42 Claims, No Drawings

STEROL EXTRACTION WITH POLAR SOLVENT TO GIVE LOW STEROL, HIGH TRIGLYCERIDE, MICROBIAL OIL

This application is a 371 of PCT/EP97/02510 filed May 5, 1997.

FIELD OF THE INVENTION

The present invention relates to purified (such as by extraction) polyunsaturated fatty acid (PUFA)-containing (microbial) oils, especially oils with a triglyceride content of at least 97% and/or a sterol content of either less than 1.5% or greater than 10%.

BACKGROUND OF THE INVENTION

There is a growing tendency to include lipid products containing polyunsaturated fatty acids derived from various fermentation processes in foodstuffs. This is of importance in the recently established desirability to incorporate certain polyunsaturated fatty acids in an infant formula.

Various processes have been described for the fermentative production of lipids or oils containing polyunsaturated fatty acids. Examples are EP-A-155,420 for the production of γ-linolenic acid (GLA)-containing lipid from Mortierella, EP-A-223,960, EP-A-276,541 and WO-A-92/13086 for the production of arachidonic acid (ARA)-containing oil from Mortierella and/or Pythium, WO-A-91/07498 and WO-A-91/11918 for the production of docosahexaenoic acid (DHA)-containing oil from *Cryptheocodinium cohnii* or Thraustochytrium, and WO-A-91/14427 for the production of eicosapentaenoic acid (EPA)-containing oil from Nitzschia. Typically, the microbial species producing the lipid containing the desired polyunsaturated fatty acid(s) is cultured in a suitable medium and the biomass is harvested before the desired lipid obtained.

To obtain a lipid concentrate which has a relatively high triglyceride content typically a nonpolar solvent for the lipid (e.g. hexane) or supercritical $CO_2$ is used in the extraction process. For example, EP-A-246,324 describes a fractional extraction process for the isolation of lipids from Mortierella, to obtain different extracts which are enriched in either polar or nonpolar (neutral) lipids. The neutral lipid extract still has, however, a relatively low triglyceride content (89.3%) and a high sterol content (9.4%). U.S. Pat. No. 4,857,329 describes an extraction process comprising the use of supercritical $CO_2$ to selectively elute neutral lipids from Mortierella biomass. However, the triglyceride content of the lipid extract does not exceed 86%.

Yamada et al, Industrial applications of single cell oils, Eds. Kyle and Ratledge, 118–138 (1992) describe an arachidonic acid-containing oil extracted from *Mortierella alpina* biomass using hexane. The purified oil has a triglyceride content of 90%.

Thus, until now it has not been possible to obtain a microbial triglyceride oil with a high triglyceride content, i.e. 95% or higher, using previous fermentation and extraction technology. It has also not been possible to prepare oils having a particularly low (e.g. less than 1.5%) or high (e.g. at least 10%) sterol content.

DESCRIPTION OF THE INVENTION

The present invention generally relates to a process for preparing a (microbial) oil with a high triglyceride content and a low content of "unsaponifiables", where an oil extracted, obtained or derived from a microbial biomass is treated with a polar solvent.

The present invention can thus provide a microbial (or microbially derived) oil having a high triglyceride content, such as $\geq 95\%$. However the oil may have a triglyceride content of at least 97%, preferably $\geq 98\%$, and optimally $\geq 99\%$. The (microbial) oil may alternatively or in addition have a low (e.g. $\leq 1.5\%$) or high (e.g. $\geq 10\%$) sterol content. Preferably the sterol content is $\leq 1\%$, such as $\leq 0.6\%$, optimally $\leq 0.3\%$.

The oil of the invention can be used in various compositions such as pharmaceutical (or therapeutic), cosmetic, feedstuff or food compositions (for human or animal consumption), especially in an infant formula or nutritional supplement.

A first aspect of the present invention therefore relates to a process of treating a microbially derived oil (an oil derived from a microorganism), the process comprising contacting the oil with a polar solvent to extract at least one compound that is soluble in the solvent, and separating at least some of the solvent containing the compound from the (so treated) oil.

The microbially derived oil can be extracted, obtained, or produced by one or more microorganism(s). Often this will be the same species of microorganism, but a mixture of two or more different microorganisms are envisaged by the invention. The process of the invention may therefore be subsequent to the production of the oil itself. The oil may be one that is produced by, or exists inside (e.g. intracellularly) the microorganism(s). Alternatively, it may be obtained from a (usually aqueous) composition obtained or resulting from fermentation (of the microorganisms). This (aqueous) composition may contain the microorganisms themselves: in that case, it is usually a fermentation broth. The microorganisms (or biomass as referred to in the art) can be removed (after fermentation) by a number of methods, for example filtration, centrifugation or decantation. The oil can be extracted or obtained from this biomass.

It is usual that the microbial oil will have been obtained by extraction. This preferably will have involved extraction using a non-polar, or preferably a water-immiscible, solvent, or at least a solvent that is capable of extracting oily components. Such a solvent may be a $C_{6-10}$ alkane, for example hexane, or (supercritical) carbon dioxide.

Different microorganisms will produce different oils. These can differ in the amount of polyunsaturated fatty acids (PUFAs) as well as in other components, and indeed the PUFAs may be in different forms, for example diglycerides, triglycerides and/or phosolipids. As such, even microbially derived oils can differ significantly from oils containing one or more of these PUFAs that have been obtained from other (e.g. animal or fish or vegetable) sources.

The microorganisms contemplated can vary widely, although preferably they will be able to produce one or more PUFAs, for example on fermentation. Microorganisms can be bacteria, algae, fungi or yeasts. Suitable fermentation processes, microorganisms and PUFA-containing oils are described in co-pending International application no. PCT/EP97/01448 (filed on Mar. 21, 1997 in the name of Gist-brocades B.V.), the content of which is incorporated herein by reference.

Preferred algae are of the genus Crypthecodinium, Porphyridium or Nitzschia. Preferred fungi are of the genus Thraustochytrium, Mortierella, Pythium, Mucorales or Entomophthora, in particular of the species *Mortierella alpina*.

The compound to be extracted can either be a desired compound, where the compound is to be purified or even isolated, or it may be an impurity that one wishes to remove from the oil. Generally speaking, the compound will fall into the latter category. Thus, the compound may be an "unsaponifiable", in other words one that is not solubilized (in water) after treatment with an alkali (e.g. NaOH) and so does not form a salt (thus it may not be capable of saponification). other compounds include sterols, which can be alicyclic alcohols having a four conjugated ring backbone, three aromatic $C_6$ rings and one cyclopentane ring (e.g. desmosterol, cholesterol) aliphatic and terpenic alcohols, tocopherol), waxes and antifoaming agents, such as polypropylene glycol, which may be present in the fermentation medium.

A second aspect of the present invention relates to a process of treating an oil comprising at least one sterol, the process comprising contacting the oil with a polar solvent to extract as least one sterol that is soluble in the solvent, and separating at least some of the solvent containing the sterol from the oil.

Preferred sterols include desmosterol, such as 5-desmosterol. If more than one sterol is present, then suitably 70 to 90%, e.g. 80 to 85%, of the sterols is desmosterol (e.g. for oil produced by Mortierella.

The oil will preferably contain at least one PUFA. This PUFA will usually have been produced by the microbe or microorganism.

A third aspect of the invention relates to a process for preparing an oil comprising at least one polyunsaturated fatty acid (PUFA), the process comprising treating an oil comprising at least one PUFA and at least one sterol with a polarsolvent to extract at least some of the PUFA and at least some of the sterol (into the solvent), both the PUFA and the sterol being at least partially soluble in the solvent, separating the solvent (phase) from the oil (phase), and evaporating or otherwise removing some of the solvent to give a (residual) oil having a sterol content of at least 10%.

This sterol content may be even higher, such as at least 11%, for example at least 14%.

PUFAs contemplated by the invention are C20 and C22 ω-3 and C18, C20 and C22 ω-6 polyunsaturated fatty acids. In particular they can include γ-linolenic acid (GLA), dihomo-γ-linolenic acid (DLA), arachidonic acid (ARA), eicosapentaenoic acid (EPA) and docosahexaenoic acid (DHA). DHA is produced by algae or fungi, such as a dinoflagellate algae, for example of the genus Crypthecodinium, or a fungus, for example of the genus Thraustochytrium. GLA, DLA or ARA can be produced by fungi, such as of the genus Mortierella, Pythium or Entomophthora. EPA can be produced by an algae, such as of the genus Porphyridium or Nitzschia. Typically the oil will dominantly or only contain one PUFA, although oils can contain one or more PUFAs, for example in a lesser amount.

In the processes of the invention after the solvent has been added to the oil, the two phases (oil and solvent) will usually separate. This can easily then allow removal of one phase from the other.

It will be realised that in the second aspect of the invention one is extracting a sterol from the oil. That can then give an oil with a low sterol content, for example no more than 1.5%. The third aspect relates to the processing of that solvent, in which some of the oil and sterol has dissolved. That solvent will thus be relatively sterol rich: after some of the solvent has been removed, one is left with a "residual" oil which can have a sterol content of at least 10%.

A fourth aspect of the invention therefore relates to an oil treated or prepared by a process according to any of the first to third aspects.

A fifth aspect relates to an oil, comprising at least one polyunsaturated fatty acid that has been produced by a microorganism, having a sterol content of no more than 1.5%. The (total) sterol content may in fact be no more than 1%, for example less than 0.6%. By using the processes of the invention, a sterol content of no more than 0.3% can be achieved.

A sixth aspect relates to an oil, comprising at least one polyunsaturated fatty acid produced by a microorganism, having a sterol content of at least 10%.

It will be realised that the oil of the fifth aspect can be prepared by using the process of this second aspect, while the oil of the sixth aspect can be prepared using the process of the third aspect.

The different oils of the invention can be prepared, for example, by using different solvents, at different temperatures, as will be described later.

The present invention therefore provides a process for preparing an (e.g. microbial) oil, where the oil is treated with one or more polar solvents. These solvent(s) can therefore remove one or more compounds that are soluble in the solvent. This may result in concentrating or enriching of the oil. Therefore, if the oil contains triglycerides, one can concentrate or increase the triglyceride content of the oil. This may be to at least 97%, for example at least 98%, and ultimately at least 99%.

Simultaneously with increasing the triglyceride content, the solvent treatment can advantageously result in the removal of one or more impurities from the oil. In particular, this treatment can result in the lowering of the amount of "unsaponifiables". These unsaponifiables that can be removed by the solvent treatment can include the sterols, aliphatic and terpenic alcohols, waxes and antifoaming agents described earlier. Usually, the treatment of the solvent will not alter the PUFA profile or the oil so treated.

The polar solvent preferably comprises a $C_{1-6}$ alkanol, for example ethanol. The solvent, however, may be an aqueous one. Preferred solvents therefore comprise an alcohol (e.g. ethanol) and water. However, the solvent may comprise other liquids, and these can be acetone and/or isopropanol.

If the solvent comprises ethanol, this may have a water content of from 0 to 20%, such as from 1 to 7%, and optionally from 2 to 4%. If the solvent comprises methanol, acetone and/or isopropanol (IPA), then the water content is preferably 0 to 2%, 5 to 50% and 5 to 15%, respectively. The solvent may therefore comprise a mixture of two or more liquids. It has been found that ethanol containing a small amount of water (e.g. 97% ethanol, 3% water) can significantly improve the yield of triglyceride after solvent treatment. This is because triglycerides are relatively insoluble in this particular solvent. Having the solvent at a temperature of from 15 to 30° C., e.g. 20 to 25° C., also reduces the amount of triglycerides that dissolved in the solvent.

By using different solvents one can vary the amount of sterol (or indeed PUFA) that is extracted. As has been discussed above, a mix of ethanol and water can provide a high yield of triglycerides since although this solvent will dissolve sterols, triglycerides are nevertheless relatively insoluble in it.

The PUFA will generally exist in several forms, such as triglycerides and diglycerides. These compounds are effectively a glycerol molecule with one or more (although usually only one) of the PUFAs attached to this backbone. Preferably the triglyceride form will be dominant. In the oil of the fifth aspect (e.g. from the process of the second aspect), the amount of diglycerides present is preferably no more than 2.2%, and preferably less than 1%. The solvent used here is preferably at a temperature of from 10 to 40° C., e.g. 20 to 30° C.

In the oil of the sixth aspect, the relative ratios of triglycerides and diglycerides can change. In the preparation of this oil, a solvent is chosen to extract not only the sterol, but also some of the triglycerides and diglycerides present in the original oil. The triglyceride content may therefore vary from 60 to 90%. The diglyceride content may vary from 5 to 25, such as from 12 to 22%. It was found that ethanol with 3% water could be a solvent for the diglycerides (and triglycerides) and so this solvent is suitable for use in the process of the third aspect, for example to produce an oil according to the sixth aspect. Here the solvent is preferably employed at a temperature of from 50 to 70° C., e.g. 55 to 65° C.

The amount of compound to be extracted, or the triglyceride content, can be adjusted by varying several process parameters. For example, one can adjust the ratio of solvent to oil, the temperature during extraction and/or by repeating the extraction process. If more than one extraction is to be performed, a counter-current extraction process is preferred, which can minimise triglyceride losses.

Usually the oil will be a crude oil obtained after extraction from a (e.g. dried) microbial biomass with a suitable solvent, followed by evaporation of that (water immiscible) solvent. The oil may be subjected to one or more refining steps prior to the process of the invention.

The oil of the invention, or one which results from a process of the first, second or third aspect, can be used for various purposes without further processing, or can be additionally subjected to one or more refining steps. The oil can be used as an additive or a supplement, for example in food compositions, such as an infant formula. It may however also be used in cosmetic or pharmaceutical compositions. The invention in a further aspect therefore relates to a composition, such as a food stuff, feed or pharmaceutical composition or a cosmetic composition, which comprises, or to which has been added, an oil of the invention. Preferred compositions are foods, such as infant formula or a nutritional supplement.

The oil of the invention can therefore have a low sterol and/or low diglyceride content. It may also have a high triglyceride content. This makes the oil particularly suitable for nutritional purposes, and can be used as a nutritional supplement. The oil may be supplied as an oil, or it may be encapsulated, for example, in a gelatin capsule. The oil can thus be incorporated in foods, feeds or foodstuffs, suitable for human or animal consumption. Suitable examples are health drinks and bread. Particularly contemplated is the use in infant formula, or in cosmetics.

Preferred features and characteristics of one aspect of the invention are equally applicable to another aspect mutatis mutandis.

The invention will now be described, by way of example, with reference to the following Examples which are provided merely for means of illustration, and are not to be construed as being limiting on the invention.

COMPARATIVE EXAMPLE 1

Recovery of crude ARA oil from *M. alpina* biomass 500 l of broth obtained after *Mortierella alpina* fermentation was filtered in a membrane filter press (cloth type: propex 46K2). The broth was filtered with a pressure difference of 0.2 bar. Within 21 minutes 500 l broth was filtered over a total filter area of 6.3 $m^2$ which resulted in an average flow of about 230 $l/m^2h$. The filter cake was washed in 30 minutes with 10 cake volumes of tap water at an average flow rate of 320 $l/m^2h$.

The cake was squeezed at 5.5 bar for 30 minutes which resulted in a dry matter content of the recovered biomass of about 45%.

Extrusion was performed on the resulting biomass cake using a single screw extruder with a profiled barrel and a universal screw. The dieplate used for extrusion had holes of diameter 2 mm.

Drying of the extrudate was performed in a fluidized bed dryer with air (8000 $Nm^3/m^2h$). The setpoint of the bed temperature was 80° C. The diameter of the dried extruded biomass was 2 mm and its dry matter content after drying was about 96%.

A crude arachidonic acid-containing oil (ARA oil) was then extracted from the extrudate using hexane as a solvent.

EXAMPLES 2 AND 3

Treatment of microbial ARA oil with 100% ethanol 5 ml of crude ARA oil was extracted from the extrudate of Example 1 with a volume of 100w ethanol for 1 minute by hand-shaking. Subsequently, the bottom and toplayers were separated by centrifugation for 5 minutes at 5000 rpm. The samples were analyzed by means of (600 Mhz) NMR (for tri- and di-glycerides, sterols (only desmosterol content measured) and antifoaming agent).

Extraction of crude ARA oil with 9 volumes of 100t ethanol at two different temperatures resulted in an oil with a decreased level of sterol and diglyceride (DG) and in an increased level of triglyceride (TG, see Table 1). The yield of TG is the percentage of triglyceride remaining in the oil after solvent extraction. Also antifoaming agent was removed and found in the ethanol after extraction. However, the yield of triglycerides was low due to the fact that some of the TG dissolved (and was thus removed in) the ethanol.

TABLE 1

Extraction of crude ARA oil with 100% ethanol (data for treated oil)

| Ex | solvent | temp. | % TG | % DG | % sterol | yield TG |
|---|---|---|---|---|---|---|
| — | Control | — | 96.2 | 2.2 | 1.6 | 100 |
| 2 | EtOH 100% | ambient | 98.2 | 0.7 | 1.1 | 73.8 |
| 3 | EtOH 100% | 60° C. | 98.5 | 0.7 | 0.8 | 43.2 |

Key:
TG: triglycerides
DG: diglycerides
Sterol: as desmosterol

EXAMPLES 4 TO 9

Treatment of microbial ARA oil with 97% ethanol

Examples 2 and 3 were repeated except using 97% ethanol at varying volumes relative to the oil.

Extraction of crude ARA oil with 1, 3 and 9 volumes of 97% ethanol resulted in an oil with a decreased level of sterol and diglyceride and in an increased level of triglyceride (see Table 2).

The yield of triglycerides was above 92% due to the fact that not much oil dissolves in 97% ethanol. At ambient temperature (about 20° C.), a higher yield of triglycerides and a better removal of diglycerides and sterols was observed. Remarkably no ethanol was found in the treated oil.

TABLE 2

Extraction of crude ARA oil with 97% ethanol
(data for treated oil)

| Ex | solvent | temp. | vol EtOH | % TG | % DG | % sterol | yield TG |
|---|---|---|---|---|---|---|---|
| — | Control | — | 0 | 96.2 | 2.2 | 1.6 | 100 |
| 4 | EtOH 97% | ambient | 1 | 96.7 | 1.8 | 1.4 | 92.9 |
| 5 | EtOH 97% | ambient | 3 | 97.8 | 1.1 | 1.1 | 95.0 |
| 6 | EtOH 97% | ambient | 9 | 98.9 | 0.4 | 0.7 | 96.2 |
| 7 | EtOH 97% | 60° C. | 1 | 96.4 | 2.0 | 1.6 | 99.7* |
| 8 | EtOH 97% | 60° C. | 3 | 97.7 | 1.1 | 1.2 | 92.4 |
| 9 | EtOH 97% | 60° C. | 9 | 98.3 | 0.6 | 1.1 | 93.7 |

Key:
TG: triglycerides
DG: diglycerides
Sterol: as desmosterol
*Due to the increase of the lower (oil) phase because the ethanol partly dissolved into the oil and so phase separation was more difficult.

The ethanol phase was also analyzed after extraction and a significant increase in sterols was observed. Also the antifoam agent (polypropylene glycol) was extracted and found in the ethanol phase (see Table 3).

TABLE 3

Extraction of crude ARA oil with 97% ethanol
(data for ethanol phase)

| Ex | solvent | temp. | vol EtOH | % TG | % DG | % antifoam | % sterol |
|---|---|---|---|---|---|---|---|
| 4 | EtOH 97% | ambient | 1 | 60.9 | 20.8 | 4.1 | 14.2 |
| 5 | EtOH 97% | ambient | 3 | 73.1 | 15.3 | 1.3 | 10.2 |
| 6 | EtOH 97% | ambient | 9 | 83.0 | 10.0 | 0.7 | 6.3 |
| 7 | EtOH 97% | 60° C. | 1 | 66.1 | 18.3 | 3.7 | 11.9 |
| 8 | EtOH 97% | 60° C. | 3 | 78.6 | 12.5 | 1.1 | 7.8 |
| 9 | EtOH 97% | 60° C. | 9 | 87.9 | 7.1 | 0.4 | 4.5 |

Key:
TG: triglycerides
DG: diglycerides
Sterol: as desmosterol

What is claimed is:

1. A process of treating an oil derived from a microorganism, the process comprising:
   (a) contacting the oil with a polar solvent to extract at least one sterol that is soluble in the solvent; and
   (b) separating at least some of the solvent containing the sterol from the oil, wherein the oil has a sterol content of less than 1.5%.

2. A process according to claim 1 when the oil is obtained or extracted from a composition resulting from a fermentation.

3. A process according to claim 2 when the composition is a fermentation broth.

4. A process according to claim 2 wherein the oil is derived, obtained or extracted from microorganisms present in the composition.

5. A process according to claim 4 wherein the microorganisms are first removed from the composition.

6. A process according to claim 5 wherein the microorganisms are first removed by filtering the composition.

7. A process according to claim 5 wherein the microorganisms are dried before the oil is obtained.

8. A process according to claim 2 wherein the oil has been extracted using a solvent for triglycerides.

9. A process according to claim 8 when the solvent is hexane, supercritical carbon dioxide or isopropanol.

10. A process according to claim 1 wherein the oil is produced by, or the microorganisms is, a bacterium, fungus, yeast or alga.

11. A process according to claim 10 when the microorganism is of the genus Crypthecodinium, Mucorales, Thraustochytrium, Mortierella, Pythium, Entomophthora, Porphyridium or Nitzschia.

12. A process according to claim 1 wherein the oil is derived from *Mortierella alpina*.

13. A process according to claim 1 wherein the sterol is produced by, or is present intracellularly inside, the microorganism.

14. A process according to claim 1 wherein the sterol is desmosterol.

15. A process according to claim 1 when the oil comprises at least one polyunsaturated fatty acid (PUFA).

16. A process according to claim 15 herein the PUFA is a C18, C20 or C22 ω-3 or ω-6 polyunsaturated fatty acid.

17. A process according to claim 16 wherein the PUFA is GLA, DLA, ARA, EPA or DHA.

18. A process for preparing an oil comprising at least one polyunsaturated fatty acid (PUFA), the process comprising:
   (a) treating an oil derived from a microorganism and comprising at least one PUFA and at least one sterol with a polar solvent to extract at least some of the PUFA and at least some of the sterol, both the PUFA and sterol being at least partially soluble in the solvent; and
   (b) separating the solvent from the oil, and evaporating or otherwise removing some of the solvent,
   to give a (residual) oil having a sterol content of at least 10%.

19. A process according to claim 18 when the sterol is desmosterol.

20. A process according to claim 18 wherein the PUFA is a C18, C20 or C22 ω-3 or ω-6 polyunsaturated fatty acid.

21. A process according to claim 20 when the PUFA is GLA, DLA, ARA, EPA or DHA.

22. A process according to claim 1 wherein the solvent comprises a $C_{1-6}$ alkanol or acetone.

23. A process according to claim 22 wherein the solvent is ethanol or isopropanol.

24. A process according to claim 1 wherein the solvent comprises ethanol and from 1% to 5% water.

25. A process according to claim 1 wherein the amount of solvent used in the extraction is from 1 to 9 times the volume of the oil to be treated.

26. A process according to claim 18 wherein the solvent comprises a $C_{1-6}$ alkanol or acetone.

27. A process according to claim 26 wherein the solvent is ethanol or isopropanol.

28. A process according to claim 18 wherein the solvent comprises ethanol and from 1% to 5% water.

29. A process according to claim 18 wherein the amount of solvent used in the extraction is from 1 to 9 times the volume of the oil to be treated.

30. An oil treated or prepared by a process according to claim 1.

31. An oil, comprising at least one polyunsaturated fatty acid (PUFA) that has been produced by a microorganism, having a sterol content of no more than 1.5%.

32. An oil according to claim 31 having a sterol content of no more than 1%.

33. An oil treated or prepared by a process according to claim 18.

34. An oil comprising at least one polyunsaturated fatty acid (PUFA) produced by a microorganism, having a sterol content of at least 10%.

35. In a pharmaceutical, cosmetic, feed or foodstuff composition for consumption by humans or animals having active ingredients wherein the improvement comprises as an active ingredient the oil according to claim 30.

36. A composition comprising, or to which has been added, an oil according to claim 30.

37. A composition according to claim 36 which is a foodstuff, feed, cosmetic or pharmaceutical composition or a nutritional supplement for consumption by humans or animals.

38. A composition according to claim 37 which is an infant formula.

39. In a pharmaceutical, cosmetic, feed or foodstuff composition for consumption by humans or animals having active ingredients wherein the improvement comprises as an active ingredient the oil according to claim 33.

40. A composition comprising, or to which has been added, an oil according to claim 33.

41. A composition according to claim 40 which is a foodstuff, feed, cosmetic or pharmaceutical composition or a nutritional supplement for consumption by humans or animals.

42. A composition according to claim 41 which is an infant formula.

* * * * *